(12) United States Patent
Bouton et al.

(10) Patent No.: US 7,452,190 B2
(45) Date of Patent: Nov. 18, 2008

(54) METHOD FOR DISCRIMINATING BETWEEN OPERATING CONDITIONS IN MEDICAL PUMP

(75) Inventors: Chad E. Bouton, Delaware, OH (US); Dale M. Radcliff, Dublin, OH (US); Steven R. Nelson, Grove City, OH (US); Clark E. Fortney, Gahanna, OH (US)

(73) Assignee: Abbott Laboratories, Abbott Park, IL (US)

( * ) Notice: Subject to any disclaimer, the term of this patent is extended or adjusted under 35 U.S.C. 154(b) by 167 days.

(21) Appl. No.: 11/503,471

(22) Filed: Aug. 11, 2006

(65) Prior Publication Data

US 2006/0275142 A1 Dec. 7, 2006

Related U.S. Application Data

(62) Division of application No. 10/624,667, filed on Jul. 22, 2003, now Pat. No. 7,104,763.

(60) Provisional application No. 60/418,914, filed on Oct. 16, 2002, provisional application No. 60/418,986, filed on Oct. 16, 2002.

(51) Int. Cl.
*F04B 49/00* (2006.01)
*A61M 1/00* (2006.01)
*A61M 35/00* (2006.01)

(52) U.S. Cl. ............................. 417/63; 604/31; 604/65; 604/67

(58) Field of Classification Search .................. 417/63, 417/413.1, 474, 478; 604/31, 65, 67, 150, 604/153
See application file for complete search history.

(56) References Cited

U.S. PATENT DOCUMENTS

| | | | |
|---|---|---|---|
| 4,927,411 A | 5/1990 | Pastrone et al. | |
| 5,190,522 A | 3/1993 | Wojcicki et al. | |
| 5,464,392 A | 11/1995 | Epstein et al. | |
| 5,554,013 A | 9/1996 | Owens et al. | |
| 6,475,178 B1 | 11/2002 | Krajewski et al. | |
| 6,485,465 B2 * | 11/2002 | Moberg et al. | 604/154 |
| 6,656,148 B2 | 12/2003 | Das et al. | |
| 6,659,980 B2 | 12/2003 | Moberg et al. | |
| 2007/0058412 A1 * | 3/2007 | Wang et al. | 365/120 |

* cited by examiner

*Primary Examiner*—Devon Kramer
*Assistant Examiner*—Patrick Hamo
(74) *Attorney, Agent, or Firm*—Jackson & Co., LLP (57) ABSTRACT

A method is disclosed for determining the operating condition of a medical pump based on data derived from a pressure sensor and a position sensor. The pressure sensor generates pressure data by sensing the force on the pumping element. The position sensor generates position data by tracking the pumping cycle and determining the position of the pumping element. The pump pressure data and pump position data are processed and the calculated results compared with a predetermined threshold value to determine the operating condition of the pump. The three main types of operating conditions of concern are the following: normal condition, where liquid is present and no leaks exist in pumping chamber; leak condition, where liquid is present but a leak exists in the pumping chamber; and air stroke condition, where the chamber contains some air.

7 Claims, 7 Drawing Sheets

METHOD FOR DISCRIMINATING BETWEEN OPERATING CONDITIONS IN MEDICAL PUMP

CROSS-REFERENCE TO RELATED APPLICATIONS

This application is a division of U.S. application Ser. No. 10/624,667, filed Jul. 22, 2003 now U.S. Pat. No. 7,104,763, which claims the benefit of U.S. Provisional Application No. 60/418,914, filed on Oct. 16, 2002, and of U.S. Provisional Application No. 60/418,986, filed on Oct. 16, 2002.

BACKGROUND OF THE INVENTION

The present invention relates to a method of determining the operating condition of a medical pump. More particularly, this invention relates to a method of determining fluid status in positive displacement fluid pumping devices for the delivery of fluids to a patient.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. Of the modern medical pumps, those incorporating a diaphragm or pump cassette are often preferred because they provide a more accurate controlled rate and volume than do other types of pumps.

A typical positive displacement pump system includes a pump device driver and a disposable cassette. The disposable cassette, which is adapted to be used only for a single patient and for one fluid delivery cycle, is typically a small plastic unit having an inlet and an outlet respectively connected through flexible tubing to the fluid supply container and to the patient receiving the fluid. The cassette includes a pumping chamber, with the flow of fluid through the chamber being controlled by a plunger or piston activated in a controlled manner by the device driver.

For example, the cassette chamber may have one wall formed by a flexible diaphragm which is reciprocated by the plunger and the driver to cause fluid to flow. The pump driver device includes the plunger or piston for controlling the flow of fluid into and out of the pumping chamber in the cassette, and it also includes control mechanisms to assure that the fluid is delivered to the patient at a pre-set rate, in a pre-determined manner, and only for a particular pre-selected time or total dosage.

The fluid enters the cassette through an inlet and is forced through an outlet under pressure. The fluid is delivered to the outlet when the pump plunger forces the membrane into the pumping chamber to displace the fluid. During the intake stroke the pump plunger draws back, the membrane covering the pumping chamber pulls back from its prior fully displaced configuration, and the fluid is then drawn through the open inlet and into the pumping chamber. In a pumping stroke, the pump plunger forces the membrane back into the pumping chamber to force the fluid contained therein through the outlet. Thus, the fluid flows from the cassette in a series of spaced-apart pulses rather than in a continuous flow.

One of the requirements for a medical pump is that it is able to detect when it is operating under certain abnormal situations and to alert the user to these problems. Specifically, the pump should detect when flow of fluid is blocked, there is no fluid in the line, there is no cassette in the pump, if the pump has primed correctly, and if the valves in the pump are sealing properly.

Previous pumps that could supply all this information used at least two sensors associated with the pump chamber or tubes to provide input to the control system. The use of multiple sensors requires more physical space on the pump and potentially results in a higher unit manufacturing cost.

It is therefore a principal object of this invention to provide methods of using single pressure sensor to discriminate between operating conditions in a medical pump.

These and other objects will be apparent to those skilled in the art.

SUMMARY OF THE INVENTION

A method is disclosed for determining the operating condition of a medical pump based on data derived from a pressure sensor and a position sensor. The pressure sensor generates pressure data is by sensing the force on the pumping element. The position sensor generates position data by tracking the pumping cycle and determining the position of the pumping element. The pump pressure data and pump position data are processed. The processed data is compared with a pre-determined threshold value to determine the operating condition of the pump. The three main types of operating conditions of concern are the following: normal condition, where liquid is present and no leaks exist in pumping chamber; leak condition, where liquid is present but a leak exists in the pumping chamber; and air stroke condition, where the chamber contains some air.

DETAILED DESCRIPTION OF THE EMBODIMENTS OF THE INVENTION

The present invention will be described as it applies to its preferred embodiment. It is not intended that the present invention be limited to the preferred embodiment. It is intended that the invention cover all modifications and alternatives that may be included within the scope of the invention as defined by the claims that follow.

It will be understood by one of ordinary skill in the art that the term medical pump as used herein includes but is not limited to enteral pumps, parenteral infusion pumps, ambulatory pumps, or any positive displacement fluid pumping device for the delivery of fluids to a patient.

Figure 7:
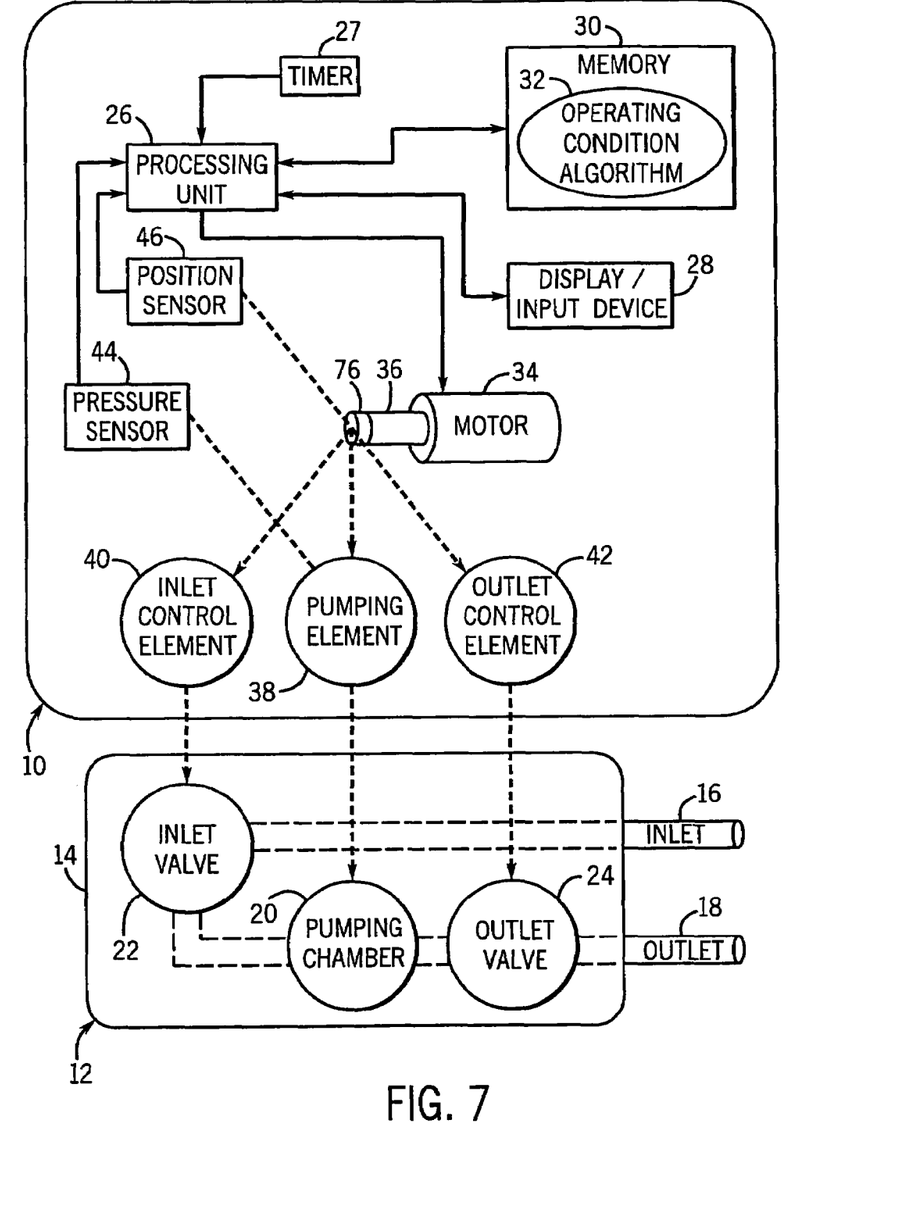
FIG. 7 is a schematic diagram of the cassette pump, illustrating the functional components of the pump and the cassette.

FIG. 7 is a schematic diagram illustrating the functional components of a medical pump 10, which is used in connection with a disposable cassette 12 for delivering a fluid to a patient. The medical pump 10 and cassette 12 are shown with several components for implementing the present invention. Those of ordinary skill in the art will appreciate that the pump 10 and cassette 12 include many more components than those shown in FIG. 7. However, it is not necessary that all these components be shown in order to disclose an illustrative embodiment for practicing the present invention.

Details of pump 10 and cassette 12 that are not discussed below can be determined by reference to commonly assigned and co-pending non-provisional application entitled MEANS FOR USING SINGLE FORCE SENSOR TO SUPPLY ALL NECESSARY INFORMATION FOR DETERMINATION OF STATUS OF MEDICAL PUMP, which claims priority from provisional applications U.S. Ser. No. 60/418,986 and 60/418,914, the disclosure and drawings of which are hereby specifically incorporated herein by reference in its entirety. This disclosure describes in detail means of using a single pressure sensor and a single position sensor to supply all necessary information to determine the status of a medical pump. The disclosures and drawings of the provisional applications U.S. Ser. No. 60/418,986 and 60/418,914 are also specifically incorporated herein by reference in their entirety. Commonly assigned and co-pending non-provisional application U.S. Ser. No. 29/166,389 entitled PUMP CASSETTE discloses the particular cassette 12 described below. Pump cassettes and cassette pumps in general are well known in the art of medical fluid delivery, as evidenced by commonly assigned U.S. Pat. Nos. 4,818,186; 4,842,584; and 5,000,664, the entire disclosure and drawings of which are hereby specifically incorporated herein by reference.

Cassette 12 includes a housing 14 on which is disposed an inlet port 16 for accepting the fluid flowing from an IV bag or other fluid container (not shown). Similarly, fluid lines (not shown) couple an outlet port 18 on housing 14 to the body of a patient.

A pumping chamber 20 is connected in fluid flow communication between the inlet port 16 and the outlet port 18. The pumping chamber 20 operates to meter fluid through the cassette 12.

An inlet valve 22 resides between inlet port 16 and the pumping chamber 20. Inlet valve 22 operates to physically open and close the fluid communication between inlet port 16 and pumping chamber 20.

Similarly, an outlet valve 24 resides between the pumping chamber 20 and outlet port 18. Outlet valve 24 operates to physically open and close the fluid communication between pumping chamber 20 and outlet port 18. The pumping chamber 20, inlet valve 22, and outlet valve 24 are all operatively associated with the pump 10 to control the flow of fluid through the cassette 12.

A processing unit 26 with a testing timer 27 is included in pump 10 and performs various operations described in greater detail below. A display/input device 28 communicates with the processing unit 26 and allows the user to receive output from processing unit 26 and/or input into the processing unit 26. Those of ordinary skill in the art will appreciate that display/input device 28 may be provided as a separate display device and a separate input device.

A memory 30 communicates with the processing unit 26 and stores code and data necessary for the processing unit 26 to calculate and output the operating conditions of pump 10. More specifically, the memory 30 stores an algorithm code 32 formed in accordance with the present invention for processing data to determine the operating condition of the pump 10.

An electric motor 34 is controlled by processing unit 26 is energized by a power supply (not shown) to serve as a prime mover for rotatably driving a shaft 36.

A pumping element 38 is operatively associated with the shaft 36. When energized, the pumping element 38 reciprocates back and forth to periodically down-stroke, causing pumping element 38 to press on pumping chamber 20, driving fluid through cassette 12. On an up-stroke, pumping element 38 releases pressure from pumping chamber 20 and thereby drawing fluid from inlet port 16 into pumping chamber 20.

An inlet control element 40 is operatively associated with the shaft 36. When energized, inlet control element 40 reciprocates back and forth to periodically down-stroke, causing inlet control element 40 to press on inlet valve 22, closing pumping chamber 20 to fluid influx. On an up-stroke, inlet control element 40 releases pressure from inlet valve 22 and thereby allows the flow of fluid from inlet port 16 into pumping chamber 20.

An outlet control element 42 is operatively associated with the shaft 36. When energized, outlet control element 42 reciprocates back and forth to periodically down-stroke, causing outlet control element 42 to press on outlet valve 24, closing pumping chamber 20 to fluid influx. On an up-stroke, outlet control element 42 releases pressure from outlet valve 24 and thereby allows the flow of fluid from pumping chamber 20 to outlet port 18. Thus the open or closed state of pumping chamber 20 is controlled by the positioning and movement of inlet and outlet control elements 40 and 42.

A pressure sensor 44 is operatively associated with the pumping element 38. The pressure sensor 44 senses the force on pumping element 38 and generates a pressure signal based on this force. The pressure sensor 44 communicates with the processing unit 26, sending the pressure signal to the processing unit 26 for use in determining operating conditions of pump 10.

One of ordinary skill in the art will appreciate that the pressure sensor 44 may be a force transducer or any other device that can operatively sense the pressure brought to bear on the pumping chamber 20 by pumping element 38.

A position sensor 46 tracks the pumping cycle of pump 10 by determining the position of the pumping element 38. The position sensor 46 can be operatively associated with the shaft 36, a cam or camshaft 76 attached to the shaft 36, or the pumping element 38 itself. The position sensor 46 generates a position signal by directly or indirectly detecting the position of the pumping element 38. For instance, in one embodiment the position sensor 46 is a Hall Effect sensor having a magnet (not shown) in relational contact with shaft 36. The rotational position of shaft 36 can be monitored to indirectly detecting the position of the pumping element 38. The position sensor 46 communicates with the processing unit 26, sending the position signal to the processing unit 26 for use in determining operating conditions of pump 10. One of ordinary skill in the art will appreciate that the position sensor 46 as used herein includes but is not limited to mechanical indicators such as pivoting dial indicators, electronic switches, Hall Effect sensors, and optical based position detectors.

In operation, at the beginning of a pumping cycle, outlet control element 42 operates to close outlet valve 24 so that there is no fluid communication between pumping chamber 20 and outlet port 18. Inlet valve 22 is opened to permit pumping chamber 20 to be in fluid communication with inlet port 16. In the next phase of the pumping cycle, inlet control element 40 operates to close inlet valve 22, thereby closing fluid communication between inlet port 16 and pumping chamber 20. Outlet valve 24 continues to remain closed. Next, pumping element 38 begins a down-stroke movement which presses pumping element 38 against pumping chamber 20, causing pumping chamber 20 to compress, thereby increasing the pressure within pumping chamber 20. Pressure sensor 44 reads and transmits this pressure data to processing unit 26. Under normal conditions pumping chamber 20 is compressed sufficiently and a desired pressure profile is generated. At a given position of shaft 36 or point in the pumping cycle, the outlet control element 42 operates to open outlet valve 24 so that fluid flows from pumping chamber 20 to outlet port 18. The pump cycle then repeats.

The processing unit 26 retrieves the operating condition algorithm 32 from memory 30 and applies it to the pressure and position data received from this pump cycle. The pump pressure data and pump position data are processed. The processed data is compared with a pre-determined threshold value to determine the operating condition of the pump. The three main types of operating conditions of concern are the following: normal condition, where liquid is present and no leaks exist in pumping chamber; leak condition, where liquid is present but a leak exists in the pumping chamber 20 (including at the inlet valve 22 or outlet valve 24); and air stroke condition, where the chamber contains some air. Once the operating condition is determined, the processing unit 26 outputs the operating condition display 28 and/or uses the determined operating condition to adjust operation of the pump 10.

One of ordinary skill in the art will understand that the threshold values for any of the algorithms disclosed herein are predetermined empirically from experimental data, and will vary from pump model to pump model.

Figure 1:
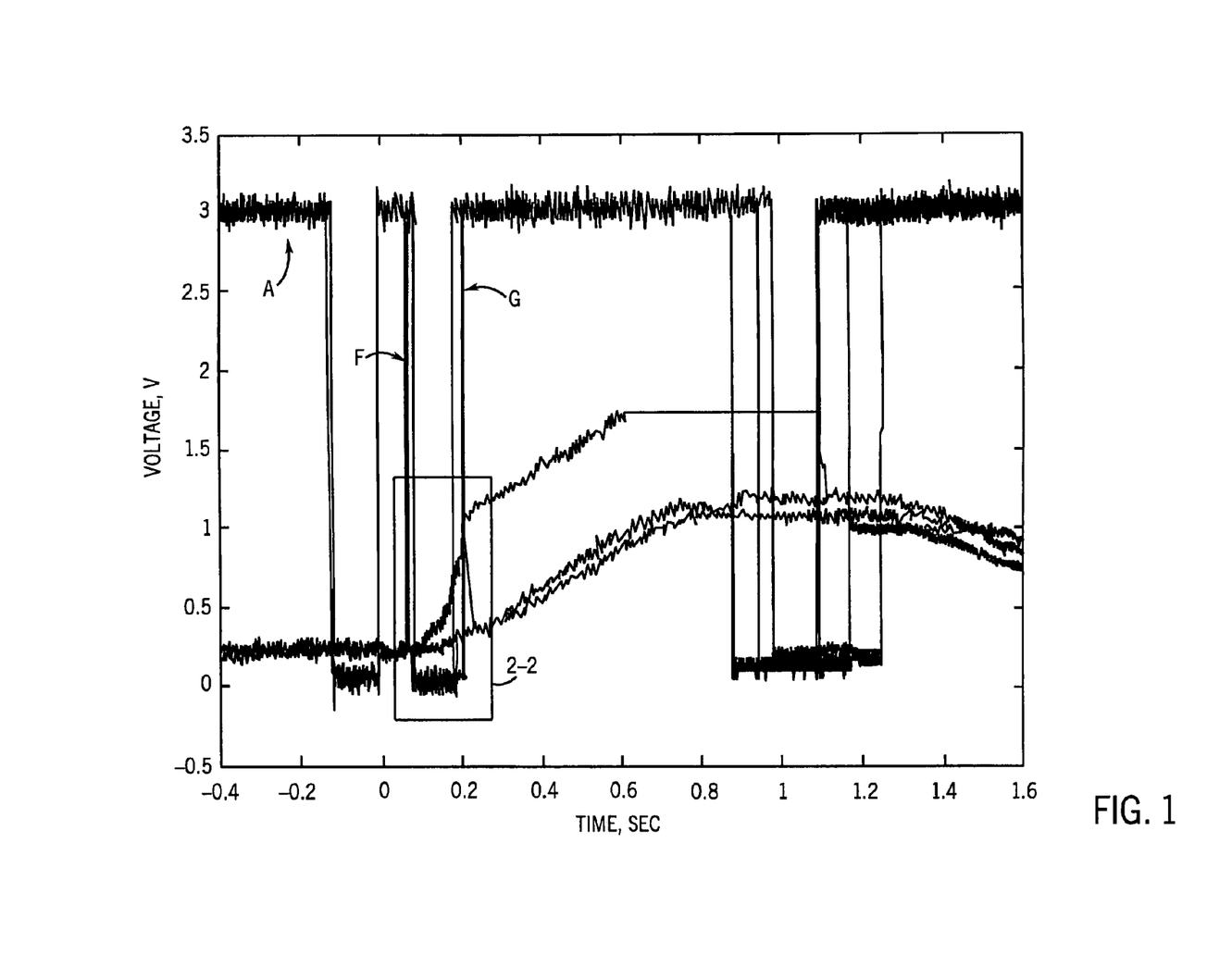
FIG. 1 is a graph showing data from a pump cycle illustrating normal, leak and air stroke conditions.

Referring to FIG. 1, the position sensor 46 is used to trigger a capture event where pressure sensor 44 data is captured for processing and operating condition discrimination. FIG. 1 shows time plots of the pressure and position signals taken with a prototype unit in the laboratory. The position signals are digital in nature and take on values near 3 or 0 V. The remaining analog signals that rise and fall more gradually are the signals that represent the pressure sensor 44 measurements. There is one pressure sensor 44 in the system and the four analog signals shown represent four different example operating conditions that have been superimposed onto the same plot. Each will be used to explain the operation of the signal processing algorithms to be disclosed.

When large amounts of data under various experimental conditions were collected, certain observations were made immediately. As shown in the example set of data shown in FIG. 1, the initial time region between −0.4 s and 0 s did not seem to offer opportunities for signal discrimination. Furthermore, other regions beyond 0.2 s also did not seem to offer signal differences that corresponded with the operating conditions of interest. Specifically, in these regions of non-interest, the back-pressure and other elements in the system seemed to dominate the pressure signal characteristics. In a region of interest, marked by line 2-2, the system is indeed operating with the pumping chamber 20 closed such that the pressure sensor 44 is detecting a building pressure during the pumping stroke. This allows unique conditions under which it may be possible to discriminate between normal, leaky, and air-filled pumping conditions.

Figure 2:
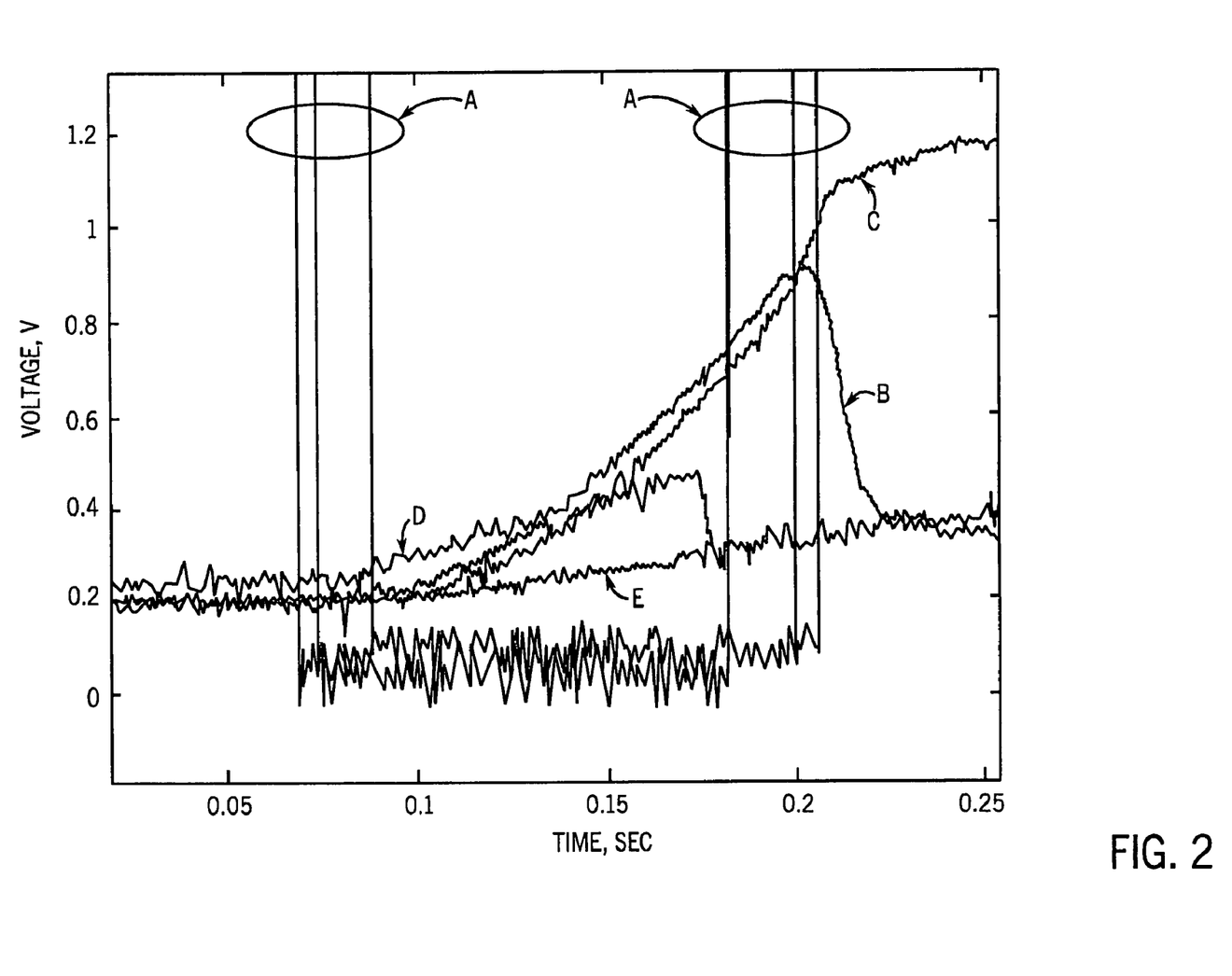
FIG. 2 is an enlarged view of the graph of FIG. 1, taken along line 2-2, showing data from a pump cycle illustrating normal, leak and air stroke conditions.

Referring to FIGS. 1 and 2, the data for the region of interest marked by line 2-2 of FIG. 1 is shown with greater detail. Pump cycle data was collected in the laboratory by subjecting a prototype pump to a wide variety of operating and environmental conditions to analyze the region of interest more closely. To develop effective and robust algorithms, it was important to analyze time shifting, bias shifts or offsets, and other variations that could occur. The four digital position signals are numbered as A and the four pressure signals are numbered B-E. The example pressure signals B-E correspond to the three previously mentioned operating condition types (Normal, Leak, and Air Stroke), and in addition a back-pressure in the system may be present. The numbered cases in the figure are as follows:

B: Normal type, no back-pressure;
C: Normal type, relatively high back-pressure present;
D: Leak type, low back-pressure; and
E: Air Stroke, low back-pressure.

Those of ordinary skill in the art will recognize that the magnitude, timing, and shape of the pressure signals may vary somewhat depending on the source or location of the leak(s), amount of air, or amount of back-pressure. For example, there are at least two more cases or combinations not shown in FIG. 2. These cases are leak type with high back-pressure and air stroke with high back-pressure.

Data for many other condition combinations were collected and analyzed, and the region of interest (shown in FIG. 1 at line 2-2 and in FIG. 2) remained the most viable one. In particular, data captured prior to a next rising edge G of the position sensor 46 proved to be an effective data set. This is due to the widely varying and uncorrelated effects that the back-pressure in the system that occurs after this rising edge G has on the pressure signal. Therefore the specific region of interest (at line 2-2) occurs between the second falling edge F of the position sensor 46 that occurs in the complete pump cycle and a time point before the next rising edge G of this position signal.

A number of algorithms were considered and tested prior to the development of the final preferred set. Among these included a simple threshold method and a method in which the falling edge of the pressure signal was analyzed (falling edge method).

The simple threshold method involved comparing the pressure signal against a predetermined threshold. However, varying signal offsets in the system reduced the performance of this method, making this method ineffective in discriminating between the operating conditions.

Figure 3:
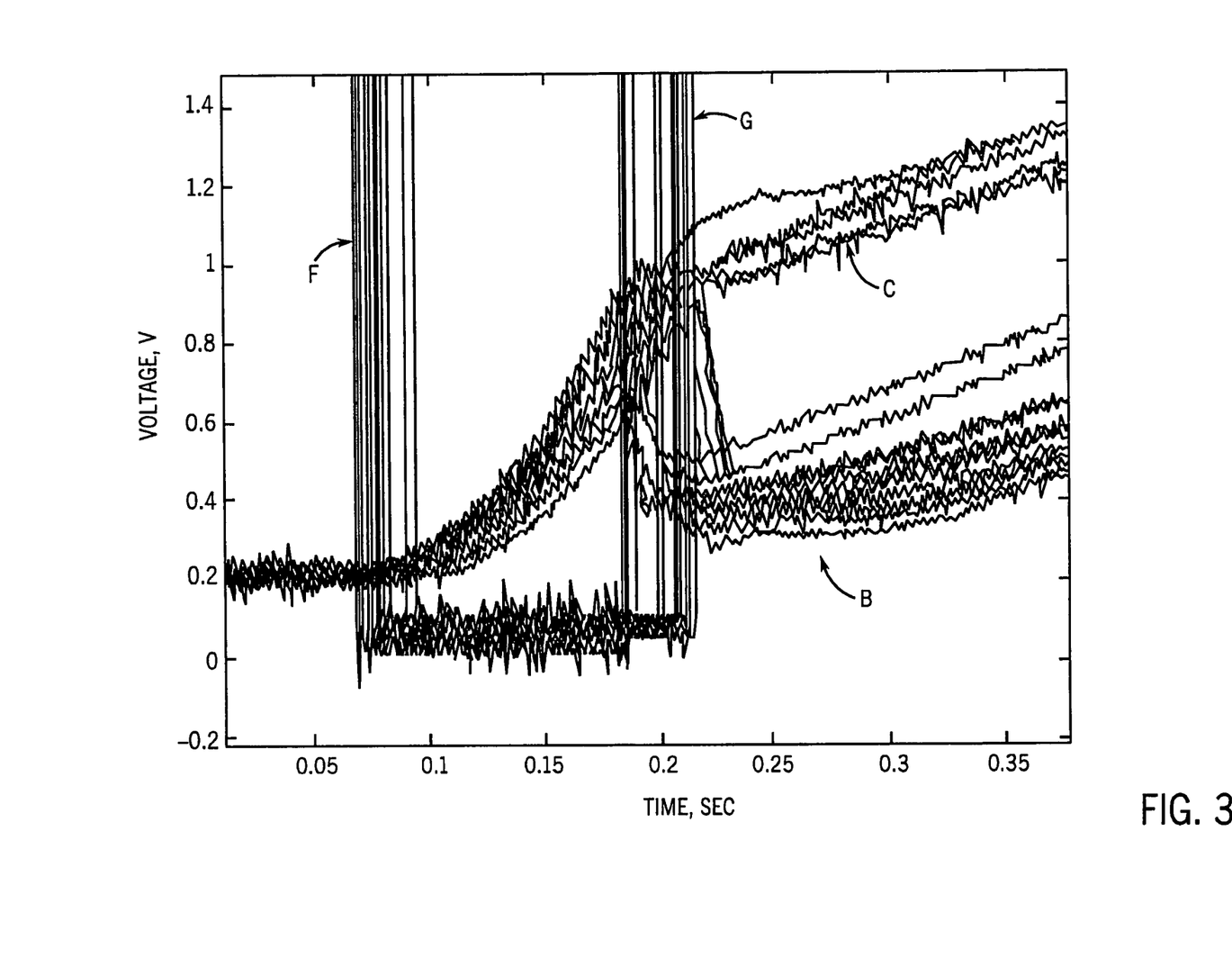
FIG. 3 is a graph showing data from a pump cycle illustrating normal stroke conditions with various back-pressure levels.

Referring to FIG. 3, in the falling edge method, the time derivative (or slope) of the data falling within the region of interest (at line 2-2 in FIG. 1) was calculated and compared to a negative threshold. With this approach a falling edge, usually typifying a normal stroke, would result in a time derivative calculation that would exceed the negative threshold. Air strokes and certain leak conditions often did not contain this falling edge characteristic and would not exceed the set threshold. However, a normal stroke with a significant back-pressure often did not have this falling edge. This can be seen in FIG. 3, where some normal type strokes do have the falling edges when the back-pressure levels are low and some do not when the back-pressure is high. This condition therefore made the falling edge method ineffective in discriminating between the operating conditions.

Other approaches and variations in the same general spirit were considered, but only the preferred approaches below will be described in detail in this disclosure. Three main embodiments of the preferred algorithms were developed and are listed as follows:

Class 1: Delayed Threshold Algorithm;
Class 2: Weighted Integration Algorithm; and
Class 3: Integrated Split Derivative Algorithm.

There are a variety of possible variations on each class of algorithm. These variations include varying the technique of weighting, disabling the weighting, position of anchor, and sequence order in which data is analyzed. The Class 1 delayed threshold algorithm is the preferred embodiment. However, the other algorithms to be described can perform equally as well under certain conditions. Therefore, all algorithms are equally important and will be discussed in equivalent detail.

Figure 4:
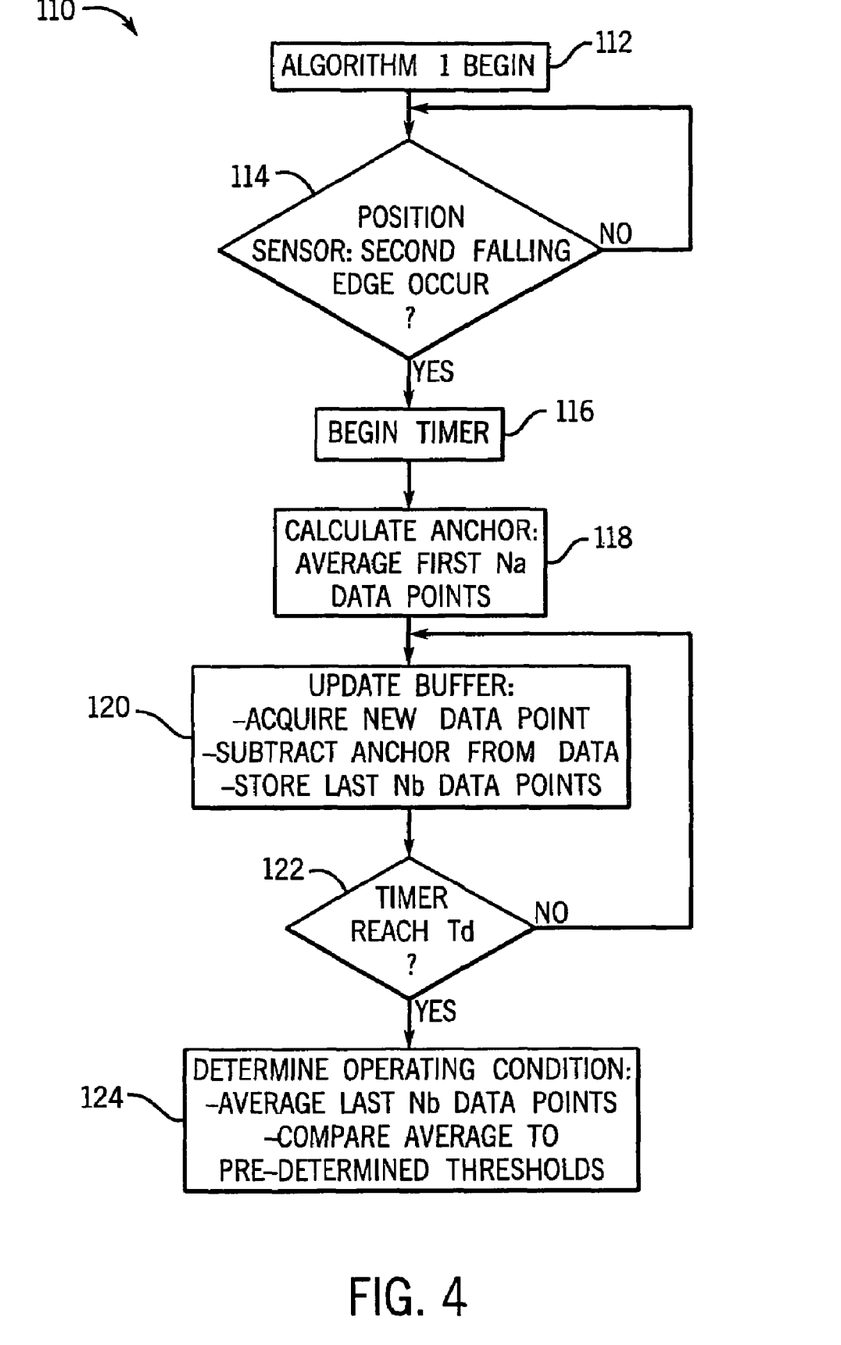
FIG. 4 is a flow chart illustrating one embodiment of determining the operating condition of a medical pump according to the present invention.

Referring to FIG. 4, the overall operation of the Class 1 algorithm 110 is shown in flowchart form. The Class 1 algorithm 110 begins at start block 112. A decision block 114 monitors the pump cycle through position signal A to determine when a region of interest is occurring. In this example, the region of interest is specified as starting when the second falling edge F of the position signal A is detected in each new pump cycle. When the second falling edge F is detected at decision block 114, the Class 1 algorithm 110 proceeds to block 116. Block 116 starts the testing timer 27 for a pre-determined test time Td. Then a block 118 acquires a plurality of pressure reference values at some pre-determined sampling rate during a first portion of test time, and once the first Na pressure reference values have been acquired a pressure anchor value is calculated and stored by averaging these pressure reference values. This anchor is stored and will be used in later calculations.

Anchoring is a technique used in this and the other algorithms as a process that removes the overall offset variation observed in the pressure signal from one pump cycle to the next and between each physical pump unit. This process involves averaging a number of the initial data points in the data set of interest and subtracting this averaged valued from all subsequent data points in the set.

A block 120 acquires a pressure data value and then calculates and stores a resultant value by subtracting the anchor value from the data value. A buffer is created and maintained for storing the last Nb resultant value samples (or data points). This buffer may be a circular buffer to improved processing efficiency. A decision block 122 shows just such a circular buffer, and repeats the steps of acquiring the pressure data value and calculating and storing the resultant value until the pre-determined test time Td has expired. Thus, as each new pressure data value is acquired the buffer is updated, until the pre-determined value of time Td has elapsed. If time Td has elapsed, then the data acquisition is complete and the final processing occurs.

During the final processing, a block 124 calculates a test value by averaging the resultant values, and compares this test value with a pre-determined threshold value to determine the operating condition of the pump. Thus, in the last step, the algorithm 110 averages the Nb data points in the storage buffer and compares this averaged value to a set of predetermined thresholds to determine the operating condition of the pump (i.e. normal, leak, or air stroke).

Figure 5:
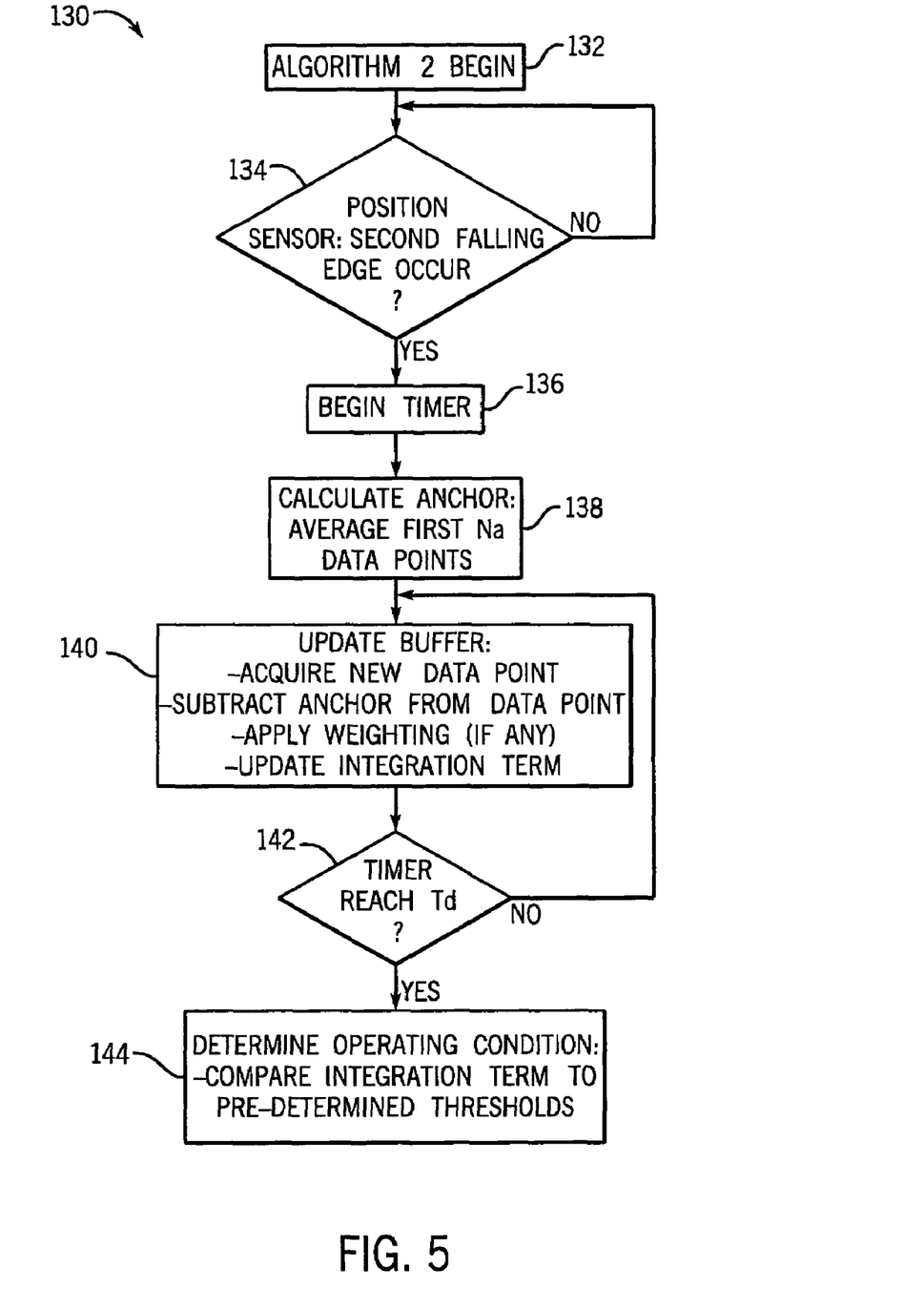
FIG. 5 is a flow chart illustrating another embodiment of determining the operating condition of a medical pump according to the present invention.

Referring to FIG. 5, the overall operation of the Class 2 weighted integration algorithm 130 is shown in flowchart form. This algorithm begins the same way as the Class 1 algorithm 130 begins, but the difference of operation lies in the update buffer and final steps.

The Class 2 algorithm 130 begins at start block 132. A decision block 134 monitors the pump cycle through position signal A to determine when a region of interest is occurring. In this example, the region of interest is specified as starting when the second falling edge F of the position signal A is detected in each new pump cycle. When the second falling edge F is detected at decision block 134, the Class 2 algorithm 130 proceeds to block 136. Block 136 starts the testing timer 27 for a pre-determined test time Td. Then a block 138 acquires a plurality of pressure reference values at some pre-determined sampling rate during a first portion of test time, and once the first Na pressure reference values have been acquired a pressure anchor value is calculated and stored by averaging these pressure reference values. This anchor is stored and will be used in later calculations.

A block 140 makes the core calculations of algorithm 130 during the buffer update to calculate an integration term. The following equation describes the integration term used in block 140:

$$I_k = I_{k-1} + (d_k - A)W(t)$$

Where $I_k$ represents the integration term, $I_{k-1}$ represents the prior integration term, $d_k$ represents the newly acquired pressure data value, A represents the anchor value, and W(t) represents the weighting value which is a function of the time (or position) at which the new pressure data value was acquired. The function W(t) can be linear, polynomial, or any other function of time to allow the emphasis and de-emphasis of various regions in the data set.

The block 140 sets a first prior integration term $I_{k-1}$ of zero when the algorithm first begins during each new pump cycle. The block 140 acquires a pressure data value $d_k$ and then calculates and stores a new integration term $I_k$ by subtracting the anchor value A from the data value $d_k$ to obtain a resultant, multiplying the resultant by a weighting value W(t) to obtain a product, and adding the product to the prior integration term $I_{k-1}$.

A decision block 142 repeats the steps of acquiring the pressure data value $d_k$ and calculating and storing the new integration term $I_k$ until the pre-determined test time Td has expired. Thus, as each new pressure data value $d_k$ is acquired the new integration term $I_k$ is updated, until the pre-determined value of time Td has elapsed. If time Td has elapsed, then the data acquisition is complete and the final processing occurs.

During the final processing, a block 144 compares the integration term $I_k$ with a pre-determined threshold value to determine the operating condition of the pump (i.e. normal, leak, or air stroke).

Figure 6:
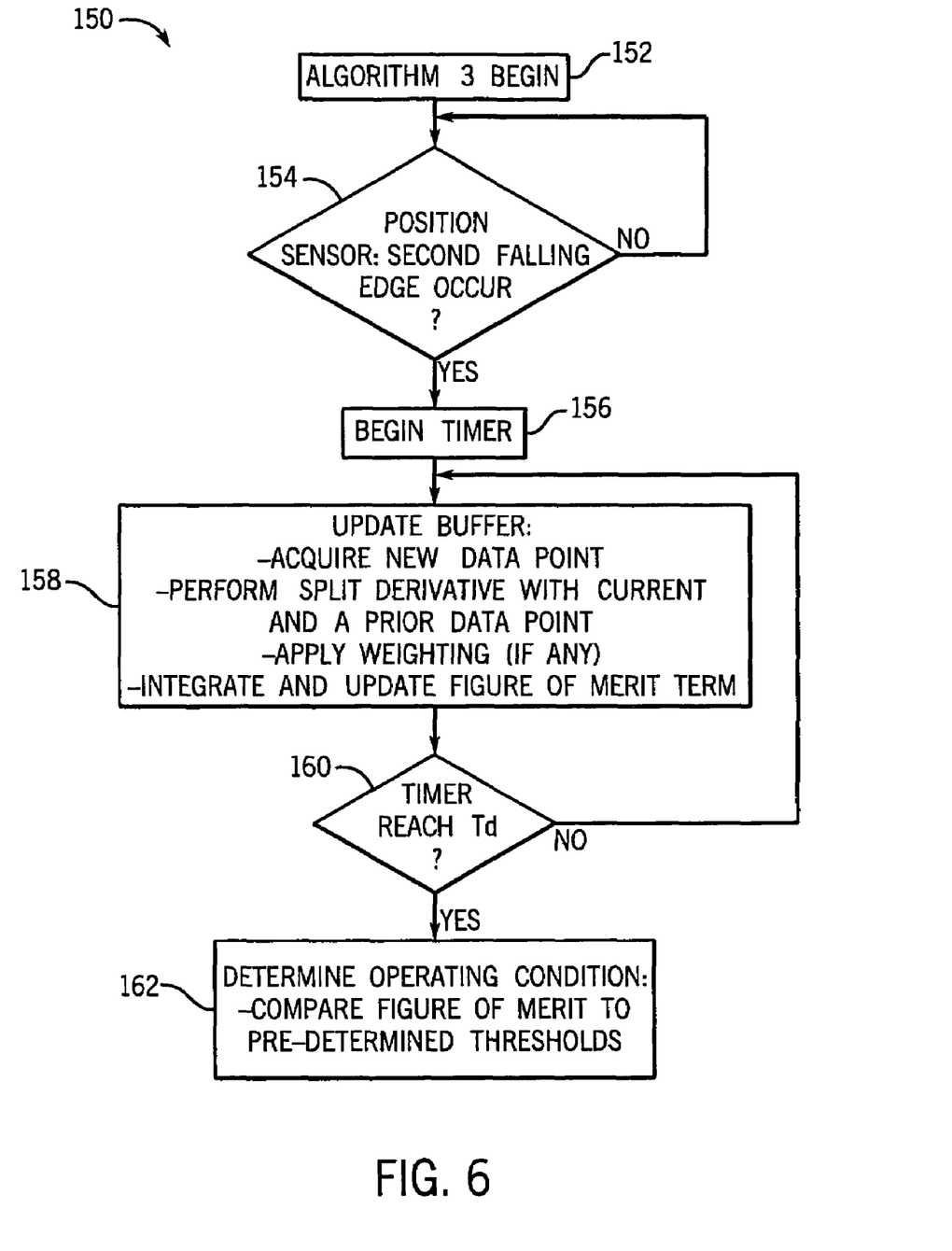
FIG. 6 is a flow chart illustrating another embodiment of determining the operating condition of a medical pump according to the present invention.

Referring to FIG. 6, the overall operation of the Class 3 integrated split derivative algorithm 150 is shown in flowchart form. The Class 3 algorithm 150 begins the same way Class 2 130 begins, but no anchor calculation is used, and the update buffer and final steps differ.

The Class 3 algorithm 150 begins at start block 152. A decision block 154 monitors the pump cycle through position signal A to determine when a region of interest is occurring. In this example, the region of interest is specified as starting when the second falling edge F of the position signal A is detected in each new pump cycle. When the second falling edge F is detected at decision block 154, the Class 3 algorithm 150 proceeds to block 156. Block 156 starts the testing timer 27 for a pre-determined test time Td.

A block 158 makes the core calculations of algorithm 150 during the buffer update to calculate a figure of merit. The following equation describes the figure of merit calculation used in block 158:

$$FOM_k = FOM_{K-1} + (d_k - d_{k-q})W(t)$$

Where $FOM_k$ represents the figure of merit, $FOM_{K-1}$ represents the prior figure of merit, $d_k$ represents the newly acquired pressure data value, $d_{k-q}$ represents any other pressure data value in the set, and W(t) represents the weighting value which is a function of the time (or position) at which the new pressure data value was acquired. The function W(t) can be a linear, polynomial, or any other function of time to allow the emphasis and de-emphasis of various regions in the data set.

The block 158 sets a first prior figure of merit $FOM_{K-1}$ of zero when the algorithm 150 first begins during each new pump cycle. The block 158 acquires the prior pressure data value $d_{k-q}$ and the new pressure data value $d_k$, where the prior pressure data value $d_{k-q}$ is any data value other than the new pressure data value. The block 158 calculates and stores a new figure of merit $FOM_k$ by subtracting the prior pressure data value $d_{k-q}$ from the new pressure data value $d_k$ to obtain a resultant, multiplying the resultant by the weighting value W(t) to obtain a product, and adding the product to the prior figure of merit $FOM_{K-1}$.

A decision block 160 repeats the steps of acquiring the new pressure data value $d_k$ and calculating and storing the new figure of merit $FOM_k$ until the pre-determined test time Td has expired. Thus, as each new pressure data value $d_k$ is acquired the new figure of merit $FOM_k$ is updated, until the pre-determined value of time Td has elapsed. If time Td has elapsed, then the data acquisition is complete and the final processing occurs.

During the final processing, a block 162 compares the figure of merit $FOM_k$ to pre-determined thresholds to determine the operating condition of the pump (i.e. normal, leak, or air stroke). For example, in one embodiment one threshold is set at 450 so that if the Figure of Merit is above 450, the pump interprets this as a normal fluid stroke; below 450, as an air stroke.

Several variations on each class of algorithms are possible which can enhance performance. These variations include varying the trigger event, technique of weighting, disabling the weighting, position of anchor, and the sequence order in which data is analyzed.

While the trigger event in the preferred embodiment is the second falling edge F of the position sensor, the trigger event can be changed to reduce system variation sensitivity as needed. The trigger event may be, for example, the second rising edge G in the pump cycle shown in FIG. 1. Setting rising edge G as the trigger event may reduce delay between the trigger event and data collection in the Class 1 algorithm 110, for example. This is important due to the fact that the Class 1 algorithm 110 will perform more satisfactorily if the pressure signal data collected correlate to a certain desired pump position. Since there is no pump element position or speed sensing available, the timer and predicted speed is used to estimate the current position. Shortening the delay between the trigger event and key data collection will reduce the accumulating effects of speed variations in the pumping motor and estimated position error, therefore increasing the probability that the collected data corresponds to the desired and anticipated position.

Another variation involves the smoothing of the data set. It is possible to acquire all data of interest before algorithm calculations begin. In this case, the data can be smoothed prior to core calculations. This is effective when the pressure signal contains undesirable noise.

The anchor location is another variable that can be changed to enhance system performance. In Class 1 algorithm 110 and Class 2 algorithm 130 embodiments the anchor is calculated by using the first Na data points. Depending on the curvature and nature of the data set, it may be advantageous to calculate this anchor by using the data points at some other location within the data set. This may accentuate a certain feature near the new anchor location and increase the discrimination level of the algorithm.

Whereas the invention has been shown and described in connection with the embodiments thereof, it will be understood that many modifications, substitutions, and additions may be made which are within the intended broad scope of the following claims. From the foregoing, it can be seen that the present invention accomplishes at least all of the stated objectives.

We claim:

1. A method for determining operating conditions in a medical pump having a cassette with a pumping chamber, comprising:
    monitoring the pump cycle with a position sensor;
    starting a testing timer for a pre-determined test time at a specified portion of the pump cycle;
    closing the pumping chamber to flow during at least a portion of the specified portion of the pump cycle;
    acquiring a plurality of pressure reference values during a first portion of test time from a single pressure sensor;
    calculating and storing a pressure anchor value by averaging the reference values;
    setting a first prior integration term of zero;
    acquiring a pressure data value from the pressure sensor;
    calculating and storing a new integration term by subtracting the anchor value from the data value to obtain a resultant, multiplying the resultant by a weighting value to obtain a product, and adding the product to the prior integration term;
    repeating the steps of acquiring the pressure data value and calculating and storing the new integration term until the pre-determined test time has expired; and
    comparing the new integration term with a pre-determined threshold value to determine the operating condition of the pump.

2. The method of claim 1, wherein the operating condition determined is normal type, leak type, or air stroke.

3. The method of claim 1, further comprising the step of smoothing the pressure reference values and pressure data values prior to performance of the calculation steps.

4. The method of claim 1, wherein the specified portion of the pump cycle is adjusted to reduce system variation sensitivity.

5. The method of claim 1, wherein the first portion of test time is adjusted to shorten the delay between the steps of starting the testing timer at the specified portion of the pump cycle and acquiring the pressure data value.

6. The method of claim 1, wherein the specified portion of the pump cycle and the first portion of test time are adjusted to vary the pressure anchor value.

7. The method of claim 1, wherein portions of the pressure reference values and pressure data values are weighted to adjust the emphasis of these portions.

* * * * *